(12) United States Patent
Ueyama et al.

(10) Patent No.: US 7,981,407 B2
(45) Date of Patent: *Jul. 19, 2011

(54) HAIR COSMETIC COMPOSITION

(75) Inventors: Kenichi Ueyama, Tokyo (JP); Nozomi Nagashima, Tokyo (JP); Kazuhisa Fukuhara, Tokyo (JP)

(73) Assignee: Kao Corporation, Tokyo (JP)

( * ) Notice: Subject to any disclaimer, the term of this patent is extended or adjusted under 35 U.S.C. 154(b) by 1024 days.

This patent is subject to a terminal disclaimer.

(21) Appl. No.: 11/061,525

(22) Filed: Feb. 22, 2005

(65) Prior Publication Data

US 2005/0201966 A1 Sep. 15, 2005

(30) Foreign Application Priority Data

Feb. 27, 2004 (JP) ................................. 2004-053710

(51) Int. Cl.
*A61Q 5/00* (2006.01)

(52) U.S. Cl. ..................................... 424/70.15; 424/70.1

(58) Field of Classification Search .......................... None
See application file for complete search history.

(56) References Cited

U.S. PATENT DOCUMENTS

| 5,403,517 | A | 4/1995 | Horinishi et al. | |
|---|---|---|---|---|
| 6,878,368 | B2 * | 4/2005 | Ohta et al. | 424/70.19 |

FOREIGN PATENT DOCUMENTS

| EP | 0 770 705 A1 | 5/1997 |
|---|---|---|
| EP | 0 978 272 A1 | 2/2000 |
| EP | 1 118 319 A1 | 7/2001 |
| EP | 1 174 112 A2 | 1/2002 |
| JP | 63-154612 | 6/1988 |
| JP | 5-178726 | 7/1993 |
| JP | 6-9347 | 1/1994 |
| JP | 6-172131 | 6/1994 |
| JP | 6-298625 | 10/1994 |
| JP | 7-112921 | 5/1995 |
| JP | 10-218738 | 8/1998 |
| JP | 11-60447 | 3/1999 |
| JP | 2000-109411 | 4/2000 |
| JP | 2003-55160 | 2/2003 |

OTHER PUBLICATIONS

Database CA 'Online!, Database Accession No. 2004:470963, XP-002333495, WO 2004/047777 A1, Jun. 10, 2004.
JP 9-301831 (Nov. 1997) Abstract.

* cited by examiner

*Primary Examiner* — Jyothsna A Venkat
(74) *Attorney, Agent, or Firm* — Oblon, Spivak, McClelland, Maier & Neustadt, L.L.P.

(57) ABSTRACT

A leave-on hair cosmetic composition, which contains the following components (A), (B) and (C):
- (A) an organic $C_{2-8}$ dicarboxylic acid or salt thereof selected from the group consisting of malonic acid, succinic acid, malic acid, or salts thereof,
- (B) at least one or more of an organic solvent selected from the group consisting of aromatic alcohols, wherein the organic solvent has a ClogP of from −2 to 3, and
- (C) an edetic acid or a salt thereof, wherein the cosmetic composition has a pH of from 2 to 5 at 25° C. when diluted to 20 times the weight with water. The present invention also relates to a hair quality improving method which includes treating the hair with the hair cosmetic composition. The hair cosmetic composition of the present invention can provide benefits such as luster, manageability, pliability and elasticity to the hair which is apt to be dry, having lost water therefrom owing to damage by coloring, permanent waving, or repetitive excessive blow drying.

4 Claims, No Drawings

HAIR COSMETIC COMPOSITION

FIELD OF THE INVENTION

The present invention relates to a leave-on hair cosmetic composition containing an organic dicarboxylic acid or salt thereof.

BACKGROUND OF THE INVENTION

In recent years, it has been said that owing to the influence of chemical treatment such as hair coloring or physical treatment by blow drying, cuticles on the hair surface peel off or the hair becomes porous by the efflux of lipids from the inside of the hair and as a result, the hair inevitably becomes excessively dry, resistant to finger combing, difficult to style and is unmanageable and lusterless.

Examples of commercially available leave-on hair cosmetic compositions mainly used now include emulsion type products such as hair cream having wax, higher alcohol and surfactant to provide the hair with manageability and protect the hair from excessive drying; and gel products having a film forming polymer (set polymer) incorporated therein. Such hair cosmetic compositions can temporarily overcome the problems such as poor manageability and excessive dryness by causing an oil or fat or a polymer to adhere to the hair surface, thereby forming a film structure, but cannot fundamentally improve the hair luster or manageability.

Some hair cosmetic compositions for improving the hair quality are known. Of these, compositions using a specific organic acid and organic solvent are known as those using a technology intended to improve hair quality by acting on the inside of the hair (refer to, for example, JP-A-1995-112921, JP-A-1994-172131, JP-A-1997-301831 and JP-A-1994-298625). These compositions promote manageability of the hair by softening the hair which is stiff and therefore, hard to handle.

SUMMARY OF THE INVENTION

In the present invention, there is thus provided a leave-on hair cosmetic composition, which contains the following components (A), (B) and (C):

(A) an organic $C_{2-8}$ dicarboxylic acid or salt thereof, (B) at least one or more of an organic solvent selected from the group consisting of aromatic alcohols, N-alkylpyrrolidones, alkylene carbonates, polypropylene glycols, lactones and cyclic ketones, wherein the organic solvent has a ClogP of from −2 to 3, and (C) an edetic acid or a salt thereof; wherein the cosmetic composition has a pH of from 2 to 5 at 25° C. when diluted to 20 times the weight with water.

In another aspect of the invention, there is also provided a hair quality improving method, which includes treating the hair with the above-described composition.

DETAILED DESCRIPTION OF THE INVENTION

The present invention relates to a leave-on hair cosmetic composition capable of providing benefits such as essentially improving the hair quality, improving luster and manageability of the hair, and providing excellent feel of the hair.

Although not wanting to be limited by theory, the present inventors have completed the present invention upon finding that the improvement in feel of the hair upon shampooing, alleviation of unfavorable feel of the hair such as stiffness of the hair after permanent waving or frictional feel upon shampooing, and improvement in strength/body and luster can be achieved when an edetic acid or a salt thereof is added to a hair cosmetic composition containing an organic dicarboxylic acid and a penetration-accelerating organic solvent, since by doing so not only is its salt-resistant performance improved but also edetic acid is adsorbed to the hair in advance which suppresses the formation of scum.

In the present invention, the term "hair quality improving" means resolving unfavorable feel of the hair and improving strength/body and luster of the hair.

The organic dicarboxylic acid to be used as Component (A) of the invention has from 2 to 8 carbon atoms and examples include malonic acid, succinic acid, glutaric acid, adipic acid, maleic acid, fumaric acid, phthalic acid, oxalic acid, malic acid and tartaric acid. Of these, those having at least 3 carbon atoms are preferred, with hydroxydicarboxylic acids such as malic acid and tartaric acid, and malonic acid and succinic acid being preferred. Among them, malic acid is preferred. Examples of the salts of these organic dicarboxylic acids include salts with an alkali metal, alkaline earth metal, ammonia and organic amine compound.

These compounds serving as Component (A) may be used in combination of two or more. The content of Component (A) in the hair cosmetic composition of the invention is preferably from 0.01 to 30 wt. %, more preferably from 0.1 to 20 wt. %, even more preferably from 0.5 to 10 wt. % in consideration of internal hair-quality improving effects (pore repairing effects and the like), set retention improving effects and manageability improving effects.

The organic solvent to be used as Component (B) of the invention is at least one or more selected from the group consisting of aromatic alcohols, N-alkylpyrrolidones, alkylene carbonates, polypropylene glycols, lactones and cyclic ketones. Preferable examples are those selected from the following (b1) to (b5).

(b1) Aromatic alcohols represented by the formula (1):

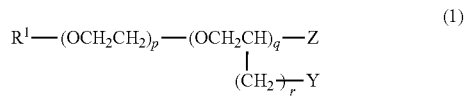

wherein, $R^1$ represents a group $R^2$-Ph-$R^3$-($R^2$: a hydrogen atom, a methyl group or a methoxy group, $R^3$: a bond or a saturated or unsaturated divalent $C_{1-3}$ hydrocarbon group, Ph: paraphenylene group), Y and Z each represents a hydrogen atom or a hydroxy group, and p, q and r each stands for an integer of from 0 to 5, with the proviso that at p=q=0, Z does not represent a hydrogen atom and $R^1$ does not represent a group $R^2$-Ph-.

(b2) N-alkylpyrrolidones having a nitrogen atom to which a $C_{1-18}$ alkyl group is bonded.

(b3) $C_{2-4}$ Alkylene carbonates.

(b4) Polypropylene glycols having a number average molecular weight of from 100 to 1000.

(b5) Lactones or cyclic ketones represented by any one of the formulas (2), (3) and (4):

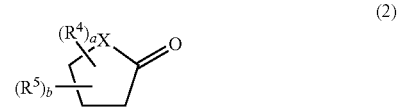

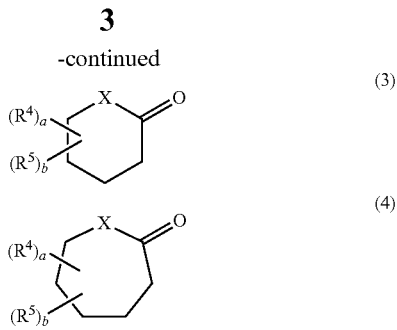

wherein, X represents a methylene group or an oxygen atom, $R^4$ and $R^5$ represent substituents which are different from each other, and a and b each stands for 0 or 1.

Of the organic solvents serving as Component (B), examples of (b1) include benzyl alcohol, cinnamyl alcohol, phenethyl alcohol, p-anisyl alcohol, p-methylbenzyl alcohol, phenoxyethanol, and 2-benzyloxyethanol; those of (b2) include N-methylpyrrolidone, N-octylpyrrolidone and N-laurylpyrrolidone; and those of (b3) include ethylene carbonate and propylene carbonate. As the polypropylene glycol (b4) having a number average molecular weight of from 100 to 1000, those having a number average molecular weight of from 100 to 500 are preferred, with those having a polymerization degree of from 2 to 5 are more preferred. In (b5), $R^4$ and $R^5$ in the formulas (2) to (4) are each preferably a linear, branched or cyclic alkyl group, hydroxy group, sulfonic acid group, phosphoric acid group, carboxy group, phenyl group, sulfoalkyl group, phosphoric acid alkyl group and carboxyalkyl group. Of these, linear or branched $C_{1-6}$ alkyl groups—such as methyl, ethyl, propyl, isopropyl and butyl—substituted at the γ position in the case of γ-lactone and substituted at the δ position (methylene adjacent to the hetero oxygen atom) in the case of δ-lactone are preferred. In order to enhance the water solubility of the compounds (2) to (4), $R^4$ or $R^5$ preferably represents an acid group such as sulfonic acid group, phosphoric acid group or carboxy group, or an alkyl group having such a group substituted therewith. In (b5), examples of the lactone include γ-butyrolactone, γ-caprolactone, γ-valerolactone, δ-valerolactone, δ-caprolactone and δ-heptanolactone. Of these, γ-lactone, especially γ-butyrolactone and γ-caprolactone are preferred in view of the stability of the lactone. Examples of the cyclic ketone as (b5) include cyclopentanone, cyclohexanone, cycloheptanone and 4-methylcycloheptanone.

Examples of the preferred Component (B) include benzyl alcohol, benzyloxyethanol, propylene carbonate and propylene glycol (number average molecular weight of from 300 to 500, especially 400).

Component (B) to be used in the invention is preferably a liquid at 25° C. and has a ClogP of from −2 to 3, preferably from −1 to 2 in view of penetration promotion. The term "ClogP" as used herein means a measure indicating the distribution of a substance between an octanol phase and an aqueous phase. It is a calculated value of an octanol-water distribution coefficient (logP) as defined by the below-described equation and its example is described in Chemical Reviews, 71(6), 1971.

$$\log P = \log([\text{Substance}]_{octanol}/[\text{Substance}]_{water})$$

wherein, [Substance]$_{octanol}$ means a mole concentration of a substance in a 1-octanol phase, while [Substance]$_{water}$ means a mole concentration of the substance in an aqueous phase.

The followings are ClogP of main compounds usable as Component (B): benzyl alcohol (1.1), 2-benzyloxyethanol (1.2), 2-phenylethanol (1.2), 1-phenoxy-2-propanol (1.1), polypropylene glycol 400 (0.9), propylene carbonate (−0.41), and Y-butyrolactone (−0.64).

As Component (B), two or more compounds may be used in combination. Its content in the hair cosmetic composition of the invention is preferably from 0.1 to 40 wt. %, more preferably from 0.5 to 10 wt. %, even more preferably from 1 to 5 wt. % in view of its feeling upon use, hair luster and hair quality improving effects (improvement of elasticity, improvement of moisture resistance, and the like).

As the salts of edetic acid serving as Component (C), alkali metal salts such as sodium salts and potassium salts can be used. Specific examples include disodium edetate, trisodium edetate and tetrasodium edetate. When edetic acid or a salt thereof is added to the hair cosmetic composition, not only is its salt-resistant performance improved but also edetic acid is adsorbed to the hair in advance which suppresses the formation of scum, resulting in the improvement in hair feel upon shampooing, alleviation of stiffness of the hair after permanent waving or unfavorable feel of the hair upon shampooing, and improvement in strength/body and luster.

As Component (C), two or more compounds may be used in combination. Its content in the hair cosmetic composition of the invention is preferably from 0.01 to 10 wt. %, more preferably from 0.05 to 5 wt. %, even more preferably from 0.1 to 2 wt. %.

A weight ratio (A):(B) of the organic dicarboxylic acid or salt thereof as Component (A) to the organic solvent as Component (B) preferably ranges from 10:1 to 1:7, more preferably from 4:1 to 1:3 in order to effectively produce internal hair-quality improving (pore repairing) effects, set retention improving effects and manageability improving effects.

The organic solvent as Component (B) and edetic acid or salt thereof as Component (C) are preferably added at a weight ratio ranging from 2000:1 to 2:1, more preferably within a range of from 500:1 to 5:1 in order to promote the penetration of Component (C) in the hair and effectively produce the improving effect of strength/body of the hair and set retention.

The hair cosmetic composition of the invention may further contain ethanol. Ethanol contributes to the solubilization or stable dispersion of Component (B). It also contributes to the solubilization of Components (A) and (C), whereby the penetration into the hair is promoted. The content of ethanol in the hair cosmetic composition of the invention is preferably from 0.01 to 50 wt. %, more preferably from 1 to 20 wt. %. A weight ratio of ethanol to Component (B) preferably ranges from 40:1 to 2:1, more preferably from 20:1 to 3:1 from the viewpoint of penetration promotion of Components (A) through (C) into the hair.

The hair cosmetic composition of the invention may further contain a set polymer in view of improvement of hair styling, regulation of viscosity, stability, improvement of adhesion upon application to the hair, improvement of feel of the hair and early expression of hair quality improving effects. Examples of such a polymer include polyvinylpyrrolidone polymer compounds such as polyvinylpyrrolidone, vinylpyrrolidone/vinyl acetate copolymer, vinylpyrrolidone/vinyl acetate/vinyl propionate tertiary copolymer, vinylpyrrolidone/alkylaminoacrylate (quaternized chloride) copolymer, vinylpyrrolidone/acrylate/(meth)acrylic acid copolymer, and vinylpyrrolidone/alkylaminoacrylate/vinylcaprolactam copolymer; acidic vinyl ether polymer compounds such as methyl vinyl ether/maleic anhydride alkyl half ester copolymer; acidic polyvinyl acetate polymer compounds such as vinyl acetate/crotonic acid copolymer, vinyl acetate/crotonic acid/vinyl neodecanoate copolymer and vinyl acetate/crotonic acid/vinyl propionate copolymer, acidic acrylic polymer compounds such as (meth)acrylic acid/(meth)acrylate copolymer, and acrylic acid/alkyl acrylate/alkylacrylamide copolymer; amphoteric acrylic polymer compounds such as N-methacryloylethyl-N,N-dimethylammonium•α-N-methylcarboxybetaine/butyl methacrylate copolymer, and hydroxypropyl acrylate/butylaminoethyl methacrylate/ acrylic octylamide copolymer; basic acrylic polymer compounds such as acrylamide/acrylate quaternary copolymer; cellulose derivatives such as cationic cellulose derivative; and chitin/chitosan derivatives such as hydroxypropyl chitosan, carboxymethyl chitin, and carboxymethyl chitosan.

These set polymers may be used either singly or in combination of two or more. Their content in the hair cosmetic composition of the invention is preferably from 0.1 to 10 wt. %, more preferably from 0.5 to 5 wt. %.

In the hair cosmetic composition of the invention, at least one or more conditioning components selected from the group consiting of silicones and oily substances can be incorporated in order to improve conditioning effects further. Examples of the silicones include dimethylpolysiloxanes, polyether-modified silicones, amino-modified silicones, carboxy-modified silicones, methylphenylpolysiloxanes, fatty acid-modified silicones, alcohol-modified silicones, aliphatic alcohol-modified silicones, epoxy-modified silicones, fluorine-modified silicones, cyclic silicones, and alkyl-modified silicones. Of these, dimethylpolysiloxanes, polyether-modified silicones and amino-modified silicones are preferred. Dimethylpolysiloxanes, polyether-modified silicones and amino-modified silicones can impart the hair with good lubricity, smoothness and moist feeling, respectively. In the invention, various silicones can be used either singly or in combination of two or more, depending on the desired performance.

As the dimethylpolysiloxane, those having a viscosity of from 5 mm$^2$/s to 10 million mm$^2$/s can be used depending on the desired feel of the hair, wherein those having a viscosity of 10 million mm$^2$/s are often supplied in the form of an emulsion. Of these, those having a viscosity falling within a range of from 5000 mm$^2$/s to 10 million mm$^2$/s are preferred, with those having a viscosity of from 50000 mm$^2$/s to 10 million mm$^2$/s being more preferred.

The term "polyether-modified silicones" is a generic name of polyoxyethylene/methylpolysiloxane copolymers and poly(oxyethylene•oxypropylene)methylpolysiloxane copolymers and those having various HLBs are known. Examples of the commercially available products thereof include "Silicone KF351A", "Silicone KF353A", "Silicone KF6008", "Silicone KF6016", "Silicone KF6011", and "Silicone KF6012" (each, trade name; product of Shin-etsu Chemical), and "SH3771C", "SH3773C", and "SH3775C" (each, trade name; product of Dow Corning Toray Silicone). As the amino-modified silicones, amodimethicone oil or an emulsion thereof is preferred. Examples of the commercially available products thereof are amodimethicone emulsion "SM8704C" (trade name; product of Dow Corning Toray Silicone) and "KT-1989" and "XF-42-B1989" (each, trade name; product of GE Toshiba Silicones).

The content of the silicones in the hair cosmetic composition of the invention is preferably from 0.05 to 20 wt. %, more preferably from 0.1 to 10 wt. %, even more preferably from 0.5 to 5 wt. % in consideration of smooth finger combing and stickiness-free feel.

The oily substance is added to improve the hair manageability after drying. Examples thereof include hydrocarbons such as squalene, squalane, liquid isoparaffin, light liquid paraffin, heavy liquid isoparaffin, α-olefin oligomer, liquid paraffin and cycloparaffin; glycerides such as castor oil, cacao oil, mink oil, avocado oil and olive oil; waxes such as bees wax, spermaceti, lanolin, microcrystalline wax, ceresin wax and carnauba wax; higher alcohols such as cetyl alcohol, oleyl alcohol, stearyl alcohol, isostearyl alcohol and 2-octyldodecanol; esters such as octyldodecyl myristate, hexyl laurate, cetyl lactate, propylene glycol monostearate, oleyl oleate, hexadecyl 2-ethylhexanoate, isononyl isononanoate and tridecyl isononanoate; higher fatty acids such as capric cid, lauric acid, myristic acid, palmitic acid, stearic acid, behenic acid, oleic acid, coconut oil fatty acid, isostearic acid and isopalmitic acid; and other oils such as isostearyl glyceryl ether and polyoxypropylene butyl ether. Of these, branched hydrocarbons including squalene, squalane, liquid isoparaffin, light liquid isoparaffin, heavy liquid isoparaffin, α-olefin oligomer are preferred.

The content of the oily substance in the hair cosmetic composition of the invention is preferably from 0.05 to 20 wt. %, more preferably from 0.1 to 10 wt. %, even more preferably from 0.5 to 5 wt. % in view of good manageability and stickiness-free feel.

In the hair cosmetic composition of the invention, a surfactant may be incorporated from the viewpoints of the stabilization of the system including the solubilization and dispersion of the solvent and improvement in the feel of the hair. As the surfactant, any one of cationic surfactant, nonionic surfactant, amphoteric surfactant and anionic surfactant can be used.

Examples of the cationic surfactant include quaternary ammonium salts represented by the following formula (6):

wherein $R^6$ and $R^7$ each independently represents a hydrogen atom, a $C_{1-28}$ alkyl group or a benzyl group, with the proviso that they do not simultaneously represent a hydrogen atom, a benzyl group or a $C_{1-3}$ lower alkyl group, and $Z^-$ represents an anion.

Either one of $R^6$ and $R^7$ preferably represents an alkyl group having from 16 to 24 carbon atoms, more preferably 22 carbon atoms, even more preferably a linear alkyl group, while the other one represents a lower $C_{1-3}$ alkyl group, preferably a methyl group. Examples of the anion $Z^-$ include halide ions such as chloride ions and bromide ions, and organic anions such as ethyl sulfate ions and methyl carbonate ions. Of these, halide ions are preferred, among which chloride ions are preferred.

As the cationic surfactant, mono(long chain alkyl) quaternary ammonium salts are preferred. Specific examples include cetyltrimethylammonium chloride, stearyltrimethylammonium chloride, arachyltrimethylammonium chloride and behenyltrimethylammonium chloride. Of these, stearyltrimethylammonium chloride and behenyltrimethylammonium chloride are preferred.

Examples of the nonionic surfactant include polyoxyalkylene alkyl ethers, polyoxyalkylene alkenyl ethers, higher fatty acid sucrose esters, polyglycerin fatty acid esters, higher fatty acid mono- or di-ethanolamides, polyoxyethylene hydrogenated castor oils, polyoxyethylene sorbitan fatty acid esters, polyoxyethylene sorbitol fatty acid esters, alkyl saccharide surfactants, alkylamine oxides, and alkylamide amine oxides.

Of these, polyoxyalkylene alkyl ethers, polyoxyethylene hydrogenated castor oil are preferred, with polyoxyethylene alkyl ethers being more preferred.

As the amphoteric surfactant, imidazoline, carbobetaine, amidobetaine, sulfobetaine, hydroxysulfobetaine, and amidosulfobetaine can be used.

Examples of the anionic surfactant include alkylbenzene sulfonates, alkyl or alkenyl ether sulfates, alkyl or alkenyl sulfates, olefin sulfonates, alkane sulfonates, saturated or unsaturated fatty acid salts, alkyl or alkenyl ether carboxylates, α-sulfone fatty acid salts, N-acylamino acid surfactants, mono- or di-phosphate surfactants and sulfosuccinates. Examples of the counterion as the anionic residue of the above-described surfactants include alkali metal ions such as sodium ion and potassium ion; alkaline earth metal ions such as calcium ion and magnesium ion, ammonium ions, alkanolamines having 1 to 3 alkanol groups with 2 or 3 carbon atoms (such as monoethanolamine, diethanolamine, triethanolamine and triisopropanolamine). Examples of the counterion as the cationic residue include halide ions such as chloride ions, bromide ions and iodide ions, methosulfate ions and saccharinate ions.

Of these, cationic surfactants are preferred in view of feel of the hair. These surfactants may be used either singly or in combination of two or more. The content of the surfactant(s) in the hair cosmetic composition of the invention is preferably from 0.01 to 10 wt. %, more preferably from 0.05 to 3 wt. % in view of stabilization of the system including solubilization of the solvent and emulsification of the oily substance.

The hair cosmetic composition of the invention may further contain a polyhydric alcohol. The polyhydric alcohol contributes to solubilization and stable dispersion of Component (B). In addition, the enhancement of the hair luster and the hair quality improving effect is accelerated by the synergistic action between the polyhydric alcohol and Component (B). Examples of the polyhydric alcohol include ethylene glycol, glycerin, sorbitol, propylene glycol, 1,3-butyleneglycol and dipropylene glycol. Of these, glycerin is preferred. These polyhydric alcohols may be used either singly or in combination of two or more. Its content in the hair cosmetic composition of the invention is preferably from 0.1 to 10 wt. %, more preferably from 0.5 to 5 wt. %.

The hair cosmetic composition of the invention may further contain, as needed, components employed for ordinary hair cosmetic compositions depending on their purpose of use. Examples of such components include antidandruffs, vitamin preparations, bactericides, anti-inflammatories, chelating agents other than Component (C), humectants such as sorbitol and panthenol, coloring agents such as dyes and pigments, viscosity regulators such as hydroxyethyl cellulose, methyl cellulose, polyethylene glycol and clay mineral, pH regulators such as organic acids other than Component (A), sodium hydroxide and potassium hydroxide, plant extracts, pearling agents, perfumes, colorants, ultraviolet absorbers, antioxidants, and the other components as described in ENCYCLOPEDIA OF SHAMPOO INGREDIENTS (MICELLE PRESS).

The hair cosmetic composition of the invention is adjusted to have a pH of from 2 to 5 (at 25° C. when diluted to 20 times the weight with water), preferably from 2.5 to 4, more preferably from 3 to 4 upon application to the hair from the standpoints of promoting penetration and adsorption of Components (A) and (B) to the hair and at the same time, giving luster, flexibility, manageability and pliability to the hair.

The form of the hair cosmetic composition of the invention can be selected from liquid, gel, paste, cream and wax as needed, but that in the form of a solution using, as a solvent, water is preferred.

The hair cosmetic composition of the invention is preferably used as a hair styling agent or hair conditioning agent. It can be provided, for example, as a pump spray, aerosol spray, pump foam, aerosol foam, gel or lotion.

By heating after application of the hair cosmetic composition of the invention to the hair, penetration of Components (A) and (B) into the hair can be accelerated. For the heating, a drier, heater or hair iron can be used. The heating temperature is preferably 60° C. or greater, especially preferably 70° C. or greater.

EXAMPLES

The present invention will hereinafter be described in further detail by examples. It should however be borne in mind that the present invention is not limited to or by them.

The pH in the below-described example and comparative compositions is a value at 25° C. when diluted to 20 times the weight with water.

Example 1

Hair cosmetic compositions as shown in Table 2 were prepared and their "setting property", "strength/body improving effect", "manageability", "feel of the hair" and "luster" were evaluated. The results are shown in Table 2.

(Evaluation Method)
Evaluation of "Setting Property"
1) Hair Bundle to be Evaluated A hair bundle of 10 cm in length, 1.5 cm in width and 1 g in weight was made using the hair of a Japanese female who's hair was had not been subjected to chemical treatment such as permanent waving and hair coloring. The hair bundle was bleached (by "Ravenus Color Appeal Inazuma Bleach"; product of Kao) twice and the resulting hair bundle was provided for the evaluation of setting property.

2) Treatment of the Hair Bundle
Pre-shampoo Evaluation (Treatment 7 Times)

The hair bundle to be evaluated was subjected to shampooing (with "Ravenus Designing Shampoo", product of Kao), towel drying, uniform application of 0.1 g of the invention or comparative compositions (which will hereinafter be called "treatment agent"), and drying for 10 minutes with hot air of 70° C. This treatment was repeated six times in total. After shampooing, towel drying and application of the treatment agent similarly, the hair bundle was wound around a rod having a diameter of 4 cm and dried for 10 minutes with hot air of 70° C.

Post-Shampoo Evaluation

The internal hair-quality improving effect was studied by evaluating the set retention after the treatment agent on the hair surface was washed away. After completion of the pre-shampoo evaluation, each hair bundle was shampooed and towel dried. Without application of the treatment agent to the hair, the hair bundle was wound around a rod having a diameter of 4 cm and dried for 10 minutes with hot air of 70° C.

3) Procedures and Criteria of Evaluation

The curled bundle was removed from the rod and a comb (ring comb) was caused to run through the bundle 20 times to disentangle it. It was suspended in a thermo-hydrostatic box (25° C. and 98% RH) to determine the set retention power. Described specifically, the length of the hair bundle thus suspended (distance from the bundled position to the end of the hair) was measured. The length of the hair bundle right after suspension was set as the set-retention percentage of 100% and the initial length of the hair bundle (10 cm) before curling was set as the set-retention percentage of 0%. A relative value (%) of the length of the hair bundle after 30 minutes, that is, a set-retention percentage after 30 minutes was determined in accordance with the following equation:

Set retention (%)=((initial length of the hair bundle)—(length of the hair bundle after 30 minutes))/ ((initial length of the hair bundle)—(length of the hair bundle right after curling))×100

Evaluation of "Strengthbody Improving Effect", "Manageability", "Feel of the Hair (Smoothness, Moistness, Softness, Stiffness, Stickiness)" and "Luster"

1) Hair Bundle to be evaluated

A hair bundle of 25 cm in length and 6 g in weight was made using the hair of a Japanese female not subjected to chemical treatment such as permanent waving and hair coloring. The hair bundle was bleached (by "Ravenus Color Appeal Inazuma Bleach"; product of Kao) twice and the resulting hair bundle was provided for the evaluation.

2) Treatment of the Hair Bundle

Pre-Shampoo Evaluation

The hair bundle to be evaluated was subjected to shampooing (with "Ravenus Designing Shampoo", product of Kao), towel drying, uniform application of 0.6 g of the treatment agent, and drying for 10 minutes with hot air of 70° C. while running a ring comb through the hair bundle. This treatment was repeated seven times in total.

Post-Shampoo Evaluation

In order to study the internal hair-quality improving effect, the hair bundle after completion of the pre-shampoo evaluation was shampooed and towel-dried, and then dried for 10 minutes with hot air of 70° C. while running a ring comb through the hair bundle.

3) Evaluation Criteria

Organoleptic evaluation by a panel of 5 experts was performed in accordance with the criteria shown in Table 1 and an average of the scores is shown in Table 2.

TABLE 1

| (Strength/body improving effects) | (Manageability) |
|---|---|
| 5: Obvious improvement in strength/body | 5: Excellent manageability |
| 4: Improvement in strength/body | 4: Some manageability |
| 3: Some improvement in strength/body | 3: Cannot be said either |
| 2: Only slight improvement in strength/body | 2: A little inferior in manageability |
| 1: No improvement in strength/body | 1: Lack of manageability |
| (Feel of the hair: smoothness) | (Feel of the hair: moist feel) |
| 5: Very Smooth | 5: Very moist |
| 4: Smooth | 4: Moist |
| 3: Cannot be said either | 3: Cannot be said either |
| 2: Slightly smooth | 2: Slightly moist |
| 1: Not smooth | 1: Not moist |
| (Feel of the hair: softness) | (Feel of the hair: stiffness) |
| 5: Very soft | 5: Not stiff |
| 4: Soft | 4: Slightly stiff |
| 3: Cannot be said either | 3: Cannot be said either |
| 2: Slightly soft | 2: Stiff |
| 1: Not soft | 1: Very stiff |
| (Feel of the hair: stickiness) | (Luster) |
| 5: Not sticky | 5: Marked improvement in luster |
| 4: Slightly sticky | 4: Improvement in luster |
| 3: Cannot be said either | 3: Cannot be said either |
| 2: Sticky | 2: No improvement in luster |
| 1: Very sticky | 1: Loss of luster |

TABLE 2

| | | Example composition | Comparative composition | | |
|---|---|---|---|---|---|
| | | 1 | 1 | 2 | 3 |
| Composition (wt. %) | Malic acid | 5.0 | 5.0 | 5.0 | — |
| | Phosphoric acid | — | — | — | 2.0 |
| | 2-Benzyloxyethanol | 2.5 | 2.5 | — | 2.5 |
| | Stearyltrimethylammonium chloride | 0.3 | 0.3 | 0.3 | 0.3 |
| | Glycerin | 1.0 | 1.0 | 1.0 | 1.0 |
| | Ethanol | 10.0 | 10.0 | 10.0 | 10.0 |
| | Disodium edetate | 0.8 | — | — | — |
| | Water | Balance | Balance | Balance | Balance |
| | Sodium hydroxide (pH regulator) | q.s. | q.s. | q.s. | q.s. |
| pH (at 25° C., when diluted to 20 times the weight with water) | | 3.7 | 3.7 | 3.7 | 3.7 |
| Pre-shampoo Evaluation | Set retention (%) | 83 | 79 | 49 | 43 |
| | Strength/body improving effects | 4.2 | 4.0 | 2.2 | 1.2 |
| | Manageability | 4.2 | 3.6 | 3.0 | 1.6 |
| | Smoothness | 4.0 | 3.4 | 2.0 | 1.2 |
| | Moist feel | 4.4 | 2.2 | 1.6 | 2.0 |
| | Softness | 3.8 | 3.4 | 1.8 | 1.2 |
| | Stiffness | 4.2 | 3.6 | 3.0 | 3.0 |
| | Stickiness | 4.4 | 3.8 | 3.0 | 3.0 |
| | Luster | 4.2 | 3.0 | 2.0 | 2.0 |
| Post-shampoo evaluation | Set retention (%) | 72 | 68 | 36 | 32 |
| | Strength/body improving effect | 4.0 | 3.4 | 1.6 | 1.6 |
| | Manageability | 3.4 | 3.0 | 1.2 | 1.2 |

The above-described results have revealed that unlike hair cosmetic compositions obtainable by the conventional technology that has not overcome the problems such as stiffness and stickiness, the composition according to the examples achieved providing a good set retention, strength/body improving effects, manageability and improved feel of the hair. Even after the removal of the components attached to the surface of the hair by shampooing, the above-described effects last. In addition, the hair quality improving effects such as elimination of pores inside of the hair were confirmed.

Example 2: (Pump Spray)

|  | (wt. %) |
| --- | --- |
| Malic acid | 4.0 |
| Stearyltrimethylammonium chloride | 0.25 |
| Glycerin | 1.0 |
| 2-Benzyloxyethanol | 2.5 |
| Propylene glycol (Mw400) | 1.0 |
| Ethanol | 4.5 |
| Disodium edetate | 0.3 |
| Perfume | 0.02 |
| Water | Balance |
| Sodium hydroxide (pH regulator) | Amount to adjust pH to 3.7 |

Example 3: (Pump Mist)

|  | (wt. %) |
| --- | --- |
| Malic acid | 3.5 |
| Malonic acid | 1.0 |
| 2-Benzyloxyethanol | 2.5 |
| N-methylpyrrolidone | 0.5 |
| Polyvinylpyrrolidone | 3.0 |
| Ethanol | 8.0 |
| Trisodium edetate | 0.5 |
| Perfume | 0.05 |
| Water | Balance |
| Sodium hydroxide (pH regulator) | Amount to adjust pH to 3.7 |

Example 4: (Hair Gel)

|  | (wt. %) |
| --- | --- |
| Malic acid | 2.5 |
| Succinic acid | 1.5 |
| Glycerin | 2.0 |
| 2-Benzyloxyethanol | 2.5 |
| γ-lactone | 0.5 |
| Hydroxyethyl cellulose | 2.0 |
| Ethanol | 8.0 |
| Disodium edetate | 0.1 |
| Trisodium edetate | 0.05 |
| Perfume | 0.05 |
| Water | Balance |
| Potassium hydroxide (pH regulator) | Amount to adjust pH to 3.7 |

Example 5: (Hair Lotion)

|  | (wt. %) |
| --- | --- |
| Malic acid | 4.0 |
| Lactic acid | 1.0 |
| Glycerin | 1.0 |
| 2-Benzyloxyethanol | 2.5 |
| Ethanol | 7.0 |
| Tetrasodium edetate | 0.2 |
| Perfume | 0.02 |
| Water | Balance |
| Sodium hydroxide (pH regulator) | Amount to adjust pH to 3.7 |

Example 6: (Hair Lotion)

|  | (wt. %) |
| --- | --- |
| Malic acid | 2.5 |
| Lactic acid | 2.5 |
| 2-Benzyloxyethanol | 2.5 |
| Propylene carbonate | 0.5 |
| Stearyltrimethylammonium chloride | 0.1 |
| Polyethylene glycol 400 | 0.45 |
| Ethanol | 4.5 |
| Disodium edetate | 0.2 |
| Trisodium edetate | 0.05 |
| Tetrasodium edetate | 0.05 |
| Perfume | 0.02 |
| Water | Balance |
| Sodium hydroxide (pH regulator) | Amount to adjust pH to 3.7 |

Example 7: (Pump Foam)

|  | (wt. %) |
| --- | --- |
| Malic acid | 2.5 |
| Lactic acid | 2.5 |
| Polyoxyethylene lauryl ether (16E.O.) | 1.0 |
| Stearyltrimethylammonium chloride | 0.1 |
| Glycerin | 1.0 |
| 2-Benzyloxyethanol | 2.5 |
| Ethanol | 5.5 |
| Disodium edetate | 0.08 |
| Perfume | 0.02 |
| Water | Balance |
| Sodium hydroxide (pH regulator) | Amount to adjust pH to 3.7 |

The invention claimed is:

1. A leave-on hair cosmetic composition comprising the following components (A), (B) and (C):
   (A) malic acid, or a salt thereof, in an amount ranging from 0.5 to 10 wt. %,
   (B) benyzloxyethanol in an amount ranging from 1 to 5 wt. %, and
   (C) an edetic acid or a salt thereof in an amount ranging from 0.1 to 2 wt. %;
   wherein the cosmetic composition has a pH of from 2 to 5 at 25° C. when diluted to 20 times its weight with water.

2. The hair cosmetic composition of claim 1, further comprising a set polymer that is a polyvinylpyrrolidone polymer compound.

3. A method for treating hair, comprising contacting hair with the leave-on hair cosmetic composition of claim 1.

4. The hair cosmetic composition of claim 1, further comprising a set polymer that is present in an amount ranging from 0.5 to 5 wt. %.

* * * * *